United States Patent
Eastman et al.

(10) Patent No.: US 6,472,385 B1
(45) Date of Patent: Oct. 29, 2002

(54) COMPOSITIONS AND METHODS TO ENHANCE CANCER CHEMOTHERAPY IN P53 DEFECTIVE TUMORS

(75) Inventors: Alan Eastman, Hanover, NH (US); Gordon W. Gribble, Norwich, VT (US)

(73) Assignee: Trustees of Dartmouth College, Hanover, NH (US)

( * ) Notice: Subject to any disclaimer, the term of this patent is extended or adjusted under 35 U.S.C. 154(b) by 0 days.

(21) Appl. No.: 09/634,684

(22) Filed: Aug. 8, 2000

Related U.S. Application Data

(60) Provisional application No. 60/147,897, filed on Aug. 9, 1999.

(51) Int. Cl.[7] .................. C07D 498/18; A61P 35/00; A61K 3/533
(52) U.S. Cl. .................. 514/211.08; 540/545
(58) Field of Search .................. 540/545; 514/211.08

(56) References Cited

U.S. PATENT DOCUMENTS

| | | | | |
|---|---|---|---|---|
| 4,877,776 A | * | 10/1989 | Murakata et al. | 514/43 |
| 4,923,986 A | * | 5/1990 | Murakata et al. | 540/545 |
| 5,043,335 A | * | 8/1991 | Kleinschroth | 514/211 |

FOREIGN PATENT DOCUMENTS

| | | | |
|---|---|---|---|
| JP | 62-155284 | | 7/1987 |
| JP | 5-1794 | | 1/1993 |
| JP | 07-224067 A2 | * | 8/1995 |
| WO | WO 94/04541 | * | 3/1994 |
| WO | WO 94/27982 | * | 8/1994 |
| WO | WO 00/42042 | * | 7/2000 |

OTHER PUBLICATIONS

Draetta et al. Annual Reports in Medicinal Chemistry 31 (1996) 241–248.*
Kasai (JPO) computer translation of Kasai (JP 7–224067), made Mar. 21, 2002.*
Andreassen et al. "2–Aminopurine overrides multiple cell cycle checkpoints in BHK cells", Proc. Natl Acad. Sci. USA 1992 89:2272–2276.
Bunch, R.T. and Eastman, A., "Enhancement of Cisplatin–induced Cytotoxicity by 7–Hydroxystaurosporine (UCN–01), a New $G_2$–Checkpoint Inhibitor [1]", Clinical Cancer Research 1996 2:791–797.
Bunch, R.T. and Eastman, A., "7–Hydroxystaurosporine (UCN–01) Causes Redistribution of Proliferating Cell Nuclear Antigen and Abrogates Cisplatin–induced S–Phase Arrest in Chinese Hamster Ovary Cells[1]", Cell Growth and Differentiation 1997 8:779–788.
Demarcq et al., "The Role of Cell Cycle Progression in Cisplatin–induced Apoptosis in Chinese Hamster Ovary Cells[1]", Cell Growth Differentiation 1994 5:983–993.
Delsite, R. and Djakiew, D. J. Androl., "Anti–Proliferative Effect of the Kinase Inhibitor K252a on Human Prostatic Carcinoma Cell Lines", 1996 17 5:481–490.
Fuse et al., "Unpredicted Clinical Pharmacology of UCN–01 Caused by Specific Binding to Human $\alpha_1$–Acid Glycoprotein", Cancer Res. 1998 58:3248–3253.
Guo et al., "Chromosome condensation induced by fostriecin does not require $p34^{cdc2}$ kinase activity and histone H1 hyperphosphorylation, but is associated with enhanced histone H2A and H3 phosphorylation", EMBO J. 1995 14:976–985.
Lau et al., "Mechanism by which caffeine potentiates lethality of nitrogen mustard", Proc. Natl Acad. Sci. USA 1982 79:2942–2946.
Lazarovici et al., $K_{252a}$ and Staurosporine Microbial Alkaloid Toxins as Prototype of Neurotropic Drugs, Adv. Exp. Med. Biol. 1996 391:367–377.
Lowinger et al., "The Total Synthesis of (±) K252a", Tetrahedron Letters 1995 36:8383–8386.
Nakamura et al., "Enhancement of X–Ray Cell Killing in Cultured Mammalian Cells by the Protein Phosphatase Inhibitor Calyculin A", Cancer Res. 1994 54:2088–2090.
O'Connor et al., "$G_2$ Delay Induced by Nitrogen Mustard in Human Cells Affects Cyclin A/cdk2 and Cyclin B1/cdc2–Kinase Complexes Differently", Chem. 1993 268:8298–8308.
Roberge et al., "Antitumor Drug Fostriecin Inhibits the Mitotic Entry Checkpoint and Protein Phosphatases 1 and 2A[1]", Cancer Res. 1994 54:6115–6121.
Sausville et al., "Clinical pharmacology of UCN–01: initial observations and comparison to preclinical models", Cancer Chemotherapy Pharmacology 1998 42:S54–.
Tam, S.W. et al., "Staurosporine Overrides Checkpoints for Mitotic Onset in BHK Cells[1]", Cell Growth Differentiation 1992 3:811–817.
Wang et al., "UCN–01: a Potent Abrogator of $G_2$ Checkpoint Function in Cancer Cells With Disrupted p53", J. Natl. Cancer Inst. 1996 88(14) :956–964.
Wood et al., "Design and Implementation of an Efficient Synthetic Approach to Furanosylated Indolocarbazoles: Total Synthesis of (+)–and (−) –K252a", Journal American Chemical Society 1997 119:9641–9651.
Yamashita et al., "Okadaic acid, a potent inhibitor of type 1 and type 2A protein phosphatases, activates cdc2/H1 kinase and transiently induces a premature mitosis–like state in BHK21 cells", EMBO J. 1990 13:4331–4338.

\* cited by examiner

Primary Examiner—Mukund J. Shah
Assistant Examiner—Thomas C McKenzie
(74) Attorney, Agent, or Firm—Licata & Tyrrell P.C.

(57) ABSTRACT

Compositions which abrogate DNA damage induced cell cycle arrest thereby enhancing the cell killing activity of DNA damaging anticancer agents for use in the treatment of cancer, and in particular, p53 defective cancers are provided.

1 Claim, No Drawings

COMPOSITIONS AND METHODS TO ENHANCE CANCER CHEMOTHERAPY IN P53 DEFECTIVE TUMORS

This application claims the benefit of U.S. Provisional Application No. 60/147,897, filed Aug. 9, 1999.

This invention was supported in part by funds from the U.S. government (NIH Grant No. CA82220) and the U.S. government may therefore have certain rights in the invention.

BACKGROUND OF THE INVENTION

Progression through the cell cycle is regulated carefully at various checkpoints to avoid proliferation when adverse conditions exist. For example, cells with damaged DNA arrest at checkpoints in the $G_1$ or S phase to prevent replication of damaged DNA or in the $G_2$ phase to prevent aberrant mitosis. The function of these checkpoints is to provide more time to repair damaged DNA prior to replication and mitosis, thereby enhancing cell survival and reducing the probability of mutation and carcinogenesis.

Anticancer agents including, but not limited to, cisplatin, irinotecan and radiation, work by causing DNA damage in tumor cells. However, this damage can result in arrest of cell cycle progression thereby providing time for the tumor cells to recover by repairing their DNA so that the tumor continues to grow. One successful approach to increase the cell killing activity of these anticancer agents is to inhibit cell cycle arrest such that cells continue to replicate and divide prior to repair of their damaged DNA.

Agents that abrogate the $G_2$ checkpoint activated by DNA damage include the methylxanthines caffeine and pentoxifylline (Lau et al. Proc. Natl Acad. Sci. USA 1982 79:2942–6; O'Connor et al. J. Biol. Chem. 1993 268:8298–8308; Demarcq et al. Cell Growth Differ 1994 5:983–93); the phosphatase inhibitors okadaic acid (Yamashita et al. EMBO J 1990 13:4331–8); fostriecin (Roberge et al. Cancer Res. 1994 54:6115–21; Guo et al. EMBO J 1995 14:976–85) and calyculin A (Nakamura et al. Cancer Res. 1994 54:2088–90); and certain protein kinase antagonists, such as staurosporine (Tam, S.W. Cell Growth Natl Acad. Sci. USA 1992 89:2272–6). However, many of these agents are too cytotoxic for clinical use.

A staurosporine analog, 7-hydroxystaurosporine (UCN-01), a potent protein kinase inhibitor, has been demonstrated at noncytotoxic doses to abrogate the $G_2$ arrest caused by the DNA damaging agent cisplatin (Wang et al. J. Natl. Can. Inst. 1996 88(14):956–64; Bunch, R. T. and Eastman, A. Clin. Can. Res. 1996 2:791–797). Further, using Chinese hamster ovary cells incubated with doses of cisplatin that cause predominantly an S-phase arrest, it has been shown that UCN-01 abrogates this S-phase arrest, causing progression of cells to $G_2$ and M and, subsequently, apoptotic cell death (Bunch, R. T. and Eastman, A. Cell Growth and Differentiation 1997 8:779–788). Abrogation of S phase arrest has also been observed in human cells. During a Phase I clinical trial of UCN-01, however, this compound bound avidly to plasma proteins thereby preventing penetration into the tumor and inhibiting activity of the compound (Fuse et al. Cancer Res. 1998 58:3248–3253; and Sausville et al. Cancer Chemotherapy Pharmacology 1998 42:S54–S59).

In the present invention, new compositions are provided which also abrogate DNA damage-induced cell cycle arrest. However, the abrogation activity of these compositions is not inhibited by binding to human plasma proteins. These compositions are believed to be particularly useful in enhancing anticancer chemotherapies in p53 defective tumors.

SUMMARY OF THE INVENTION

An object of the present invention is to provide ompositions comprising formula (I):

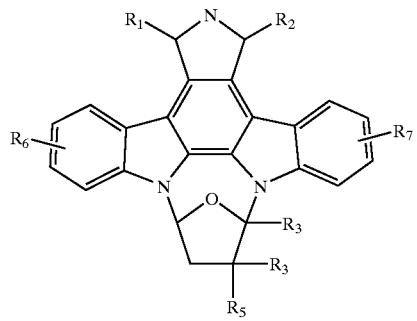

wherein $R_1$ and $R_2$ are each OH, O, $OCH_3$, $OC_2H_5$, $OC_6H_5$, $OCH_2C_6H_5$ or a related alkyl group; and $R_3$, $R_4$, $R_5$, $R_6$ are each selected from a group consisting of H, $CH_3$, $C_2H_5$, COOH, $CONH_2$, CHO, $COCH_3$, $COOCH_3$, $CH_2NHCH_3$, OH, $OCH_3$, $OC_2H_5$, $NH_2$, NHR' and $NNR'_2$, wherein R' is an alkyl group.

Another object of the present invention is to provide a method of abrogating DNA damage induced cell cycle arrest in cells comprising administering to cells a composition comprising formula (I).

Another object of the present invention is to provide a method of enhancing the cell killing activity of DNA damaging anticancer agents comprising administering in combination with the DNA damaging anticancer agent a composition comprising formula (I).

Yet another object of the present invention is to provide a method for treating cancer comprising administering to a patient suffering from cancer an anticancer agent which induces DNA damage of tumor cells and a composition comprising formula (I).

DETAILED DESCRIPTION OF THE INVENTION

The present invention relates to a novel family of compositions which abrogate DNA damage-induced cell cycle arrest without untoward binding to human plasma proteins. Compositions of the present invention comprise a ring structure similar to that of the kinase inhibitor, K252a. The structure of K252a is shown below.

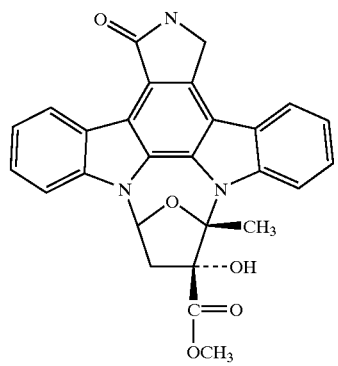

The K252a family of alkaloid toxins-kinase inhibitors are some of the most widely used compounds in biological research on the role of protein kinases in cellular transduction systems, biological functions and pathophysiology of neurological disorders (Lazarovici et al. Adv. Exp. Med. Biol. 1996 391:367–77). Members of the K252a family have been demonstrated to inhibit a number of neurotrophin-mediated cellular responses, and to preferentially inhibit the activity of neurotrophin-mediated receptors. K252a has also been demonstrated to inhibit the growth of human prostate carcinoma cells (Delsite, R. and Djakiew, D. J. Androl. 1996 17(5):481–90). K252 derivatives with protein C kinase inhibition activity have also been disclosed to be useful in the treatment or prophylaxis of circulatory system disorders, inflammation, allergies and tumors (JP 62155284; JP 93001794).

K252a has a similar ring structure to staurosporine and the staurosporine analog, UCN-01. However, in K252a the hexose. moiety is replaced with a pentose moiety. Unlike staurosporine and UCN-01, it has now been found that activity of K252a is not inhibited by addition of human plasma proteins. It is believed that the pentose ring of this structure prevents binding of this compound to human plasma proteins. However, K252a only abrogates cell cycle arrest in the S phase. K252a does not abrogate cell cycle arrest in the $G_2$ phase. In fact, K252a, when used alone, actually causes $G_2$ arrest.

It has now been found, however, that modifying the basic ring structure of K252a at carbon 7 prevents both cytotoxicity and cell cycle arrest. It has also now been found that maintenance of the pentose moiety in this ring structure results in compounds which do not bind or bind only weakly to human plasma protein.

Accordingly, the present invention relates to compositions comprising a structure as depicted in formula (I):

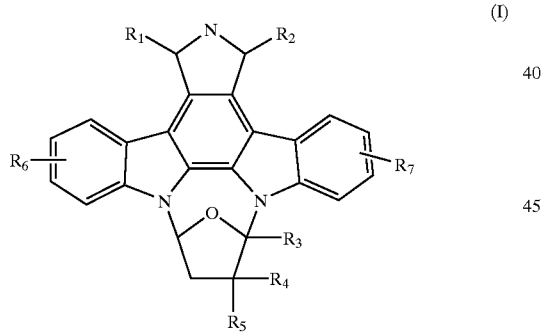

(I)

In this composition, $R_1$ and $R_2$ are preferably each selected from the group consisting of OH, O, $OCH_3$, $OC_2H_5$, $OC_6H_5$, $OCH_2C_6H_5$ or a related alkyl group. $R_3$, $R_4$, $R_5$, $R_6$ and $R_7$ are preferably each selected from the group consisting of H, $CH_3$, $C_2H_5$, COOH, $CONH_2$, CHO, $COCH_3$, $COOCH_3$, $CH_2NHCH_3$, OH, $OCH_3$, $NH_2$, NHR' and $NR'_2$, wherein R' is an alkyl group. However, as will be obvious to those of skill in the art upon this disclosure, other groups which produce compositions of similar activity can also be substituted at these positions on the ring structure.

Several exemplary compositions comprising these critical features have been synthesized. These include ICP1 having the structure of formula (II), ICP2(a,b) having the structure of formula (III), and ICP3(a,b) having the structure of formula (IV), respectively:

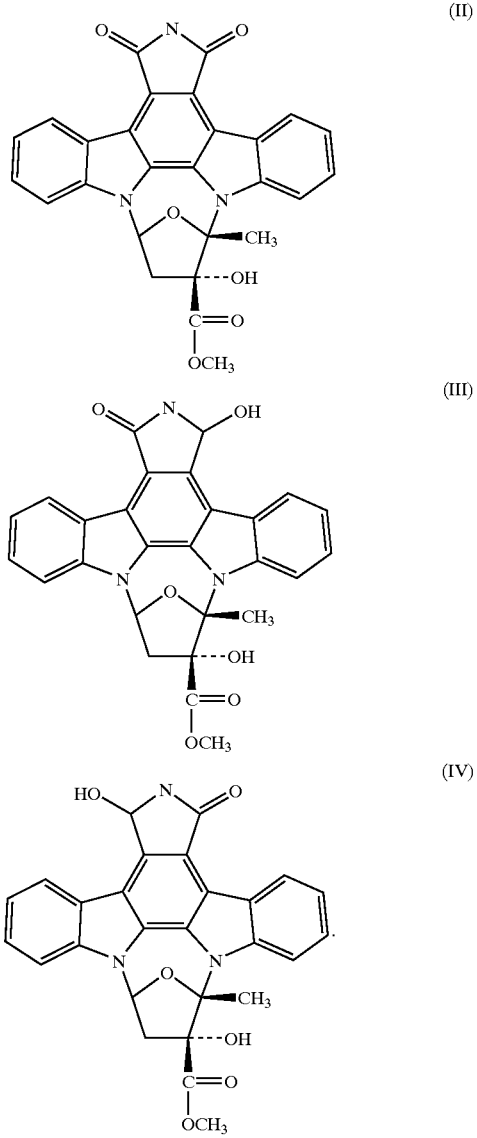

Further, using ICP1, it has now been demonstrated that a composition comprising formula (I) abrogates cell cycle arrest at non-toxic concentrations. Unlike K252a, this composition of the present invention does not cause $G_2$ arrest at concentrations capable of abrogating arrest. Further, ICP1 was demonstrated to maintain its ability to abrogate cell cycle arrest in the presence of human plasma. Thus, unlike staurosporine and UCN-01, activity of the compositions of the present invention is not limited by binding to plasma proteins. Experiments of cell cycle analysis were conducted in accordance with procedures described by Demarcq et al. Cell Growth and Differ. 1994 5:983–993; Bunch, R. T. and Eastman, A. Clinical Cancer Research 1996 2:791–7; and Bunch, R. T. and Eastman, A. Cell Growth and Differ. 1997 8:779–788.

Using ICP1, the ability of a composition of formula (I) to abrogate cell arrest has also been shown to be selective for p53 defective cell lines. Two p53 defective human breast cancer cells lines, MDA-MD-231 and T47D, were used to demonstrate this selectivity. The breast cancer cell lines were obtained from the American Type Culture Collection (Rockville, Md.). The cells were maintained in Dulbecco's modified Eagle's Medium supplemented with 10% fetal bovine serum, penicillin (100 units/ml), streptomycin (100 μg/ml) and fungizone (0.25 μg/ml).

Accordingly, the present invention provides compositions comprising formula (I) and methods of using these compositions to abrogate DNA damage induced cell cycle arrest in cells, and in particular in p53 defective cells. Abrogation of DNA damage induced cell arrest enhances the efficacy of DNA damaging anticancer agents. Thus, in one embodiment of the present invention, a composition comprising formula (I) is administered in combination with a DNA damaging anticancer agent to enhance the efficacy of the anticancer agent. By "in combination" it is meant that the composition of the present invention is administered simultaneously or just prior to or after administration of the anticancer agent. Compositions of the present invention are thus useful in methods for treating cancer wherein a patient suffering from cancer is administered an anticancer agent which induces DNA damage of tumor cells in combination with a composition comprising formula (I).

The following nonlimiting examples are provided to further illustrate the instant invention.

EXAMPLES

Example 1
Synthesis of Compositions of Formula (I)

The overall synthetic plan for these compositions is performed in accordance with methods disclosed by Lowinger et al. Tetrahedron Letters 1995 36:8383–86 and Wood et al. Journal American Chemical Society 1997 119:9641–51 in which two halves of the proposed analogs are synthesized separately. Thus, for example for ICP2(a,b) and ICP3(a,b), the 7-hydroxy-K252c and the carbohydrate were synthesized separately and subsequently condensed to create the desired 7-hydroxy-K252a analog. Synthesis of 7-hydroxy-K252c is depicted in the following scheme I.

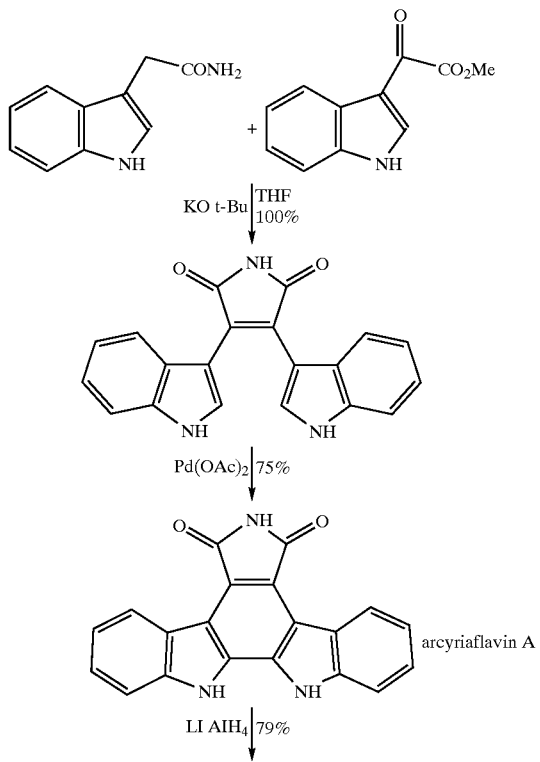

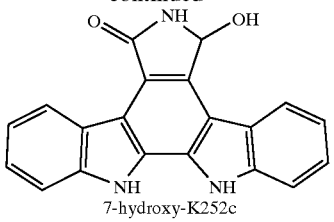
7-hydroxy-K252c

The glycoside portion of the composition is then prepared in accordance with the method of Lowinger et al. Tetrahedron Letters 1995 36:8383–86. As depicted in the following scheme II, the mixture of dimethyl glycoside is condensed with 7-hydroxy-K252c to produce a racemic mixture of 7-hydroxy-K252a (ICP2(a,b)) and 7-hydroxy-isoK252a (ICP3(a,b)).

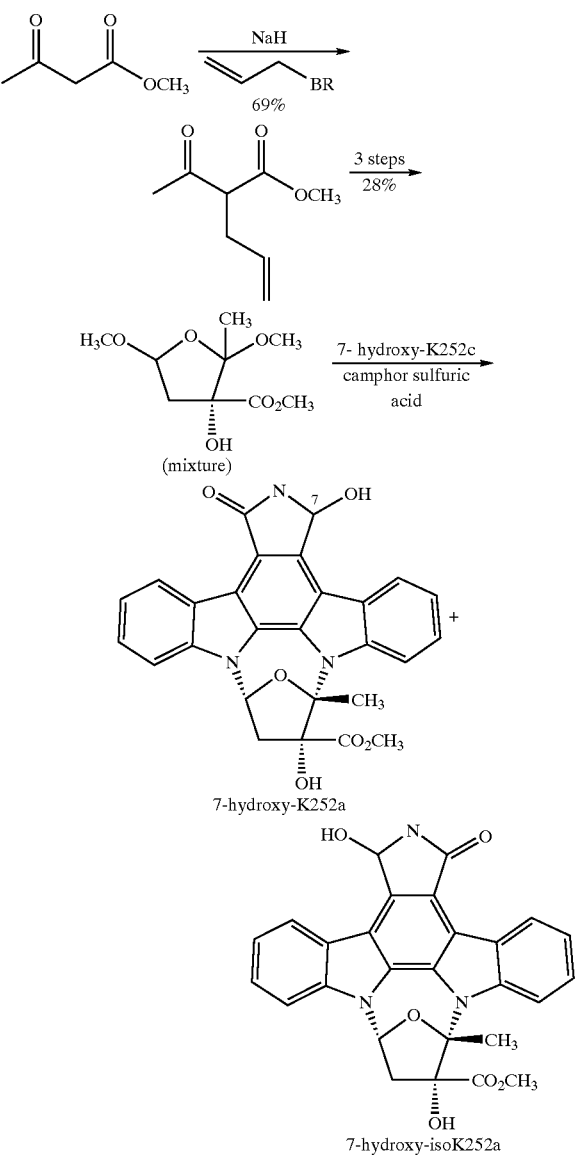

ICP1 is synthesized similarly to ICP2 and ICP3 except that the dimethyl glycoside as shown in Scheme I is condensed with arcyriaflavin A.

Example 3
Derivatives of $R_3$, $R_4$ and $R_5$ Made During the Synthesis Additional novel derivatives can also be prepared. For example, related intermediate compounds, arcyriaflavin B, C and D are naturally produced compounds with modifications in the rings at $R_6$ and $R_7$ positions. The synthetic route for these derivatives begins with a halide or other group at the appropriate position of compound 6 in the following synthetic route.

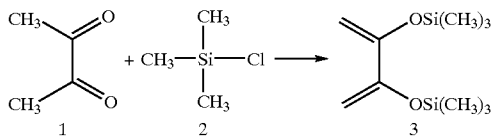

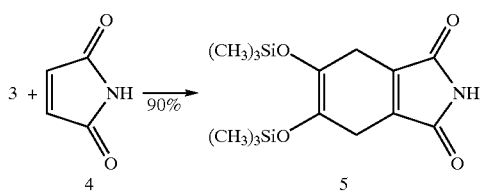

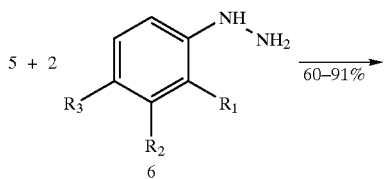

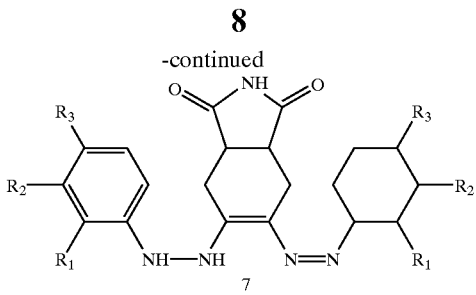

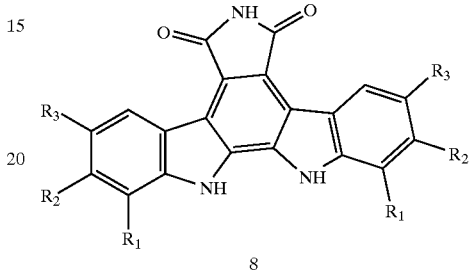

Where $R_1 R_2 R_3$ can equal one of the following: H, Cl, Br, or an O-alkyl group as described herein.

What is claimed is:

1. A method of inhibiting growth of breast cancer cells comprising contacting breast cancer cells with a compound capable of abrogating DNA damage induced cell cycle arrest in said cells wherein said compound is N(12), N(13)-(3-Hydroxy-2-methyltetrahydrofuran-3-carboxylic acid methyl ester-2,5)-5-hydroxy-K252c (ICP3(a,b)) so that DNA damage induced cell cycle arrest is abrogated and the abrogation of DNA damage induced cell cycle arrest results in an inhibition of growth of said breast cancer cells.

\* \* \* \* \*

UNITED STATES PATENT AND TRADEMARK OFFICE
CERTIFICATE OF CORRECTION

PATENT NO.        : 6,472,385 B1
APPLICATION NO.   : 09/634684
DATED             : October 29, 2002
INVENTOR(S)       : Alan R. Eastman and Gordon W. Gribble It is certified that error appears in the above-identified patent and that said Letters Patent is hereby corrected as shown below:

In the Specification

At Column 1, please delete Lines 7 - 10 and insert in its place the following:
--This invention was made with government support under grant number CA082220 awarded by the National Institutes of Health. The government has certain rights in the invention.--

Signed and Sealed this
Fifteenth Day of September, 2020

Andrei Iancu
*Director of the United States Patent and Trademark Office*